(12) United States Patent
Lee et al.

(10) Patent No.: US 10,545,079 B2
(45) Date of Patent: Jan. 28, 2020

(54) PORTABLE BLOOD VISCOSITY MEASUREMENT APPARATUS

(71) Applicant: INDUSTRIAL COOPERATION FOUNDATION CHONBUK NATIONAL UNIVERSITY, Jeonju-si, Jeollabuk-do (KR)

(72) Inventors: Donghwan Lee, Jeonju-si (KR); Jinmu Jung, Jeonju-si (KR); Jongho Park, Jeonju-si (KR); Euiho Lee, Jeonju-si (KR); Uiyun Lee, Jeonju-si (KR)

(73) Assignee: INDUSTRIAL COOPERATION FOUNDATION CHONBUK NATIONAL UNIVERSITY, Jeonju-si (KR)

( * ) Notice: Subject to any disclaimer, the term of this patent is extended or adjusted under 35 U.S.C. 154(b) by 115 days.

(21) Appl. No.: 15/778,141

(22) PCT Filed: Nov. 24, 2016

(86) PCT No.: PCT/KR2016/013623
§ 371 (c)(1),
(2) Date: May 22, 2018

(87) PCT Pub. No.: WO2017/091006
PCT Pub. Date: Jun. 1, 2017

(65) Prior Publication Data
US 2018/0340876 A1    Nov. 29, 2018

(30) Foreign Application Priority Data
Nov. 24, 2015  (KR) .................. 10-2015-0164608

(51) Int. Cl.
*G01N 11/04* (2006.01)
*G01F 23/02* (2006.01)
(Continued)

(52) U.S. Cl.
CPC ............. *G01N 11/04* (2013.01); *G01F 23/02* (2013.01); *G01F 23/292* (2013.01); *G01N 33/49* (2013.01); *G01N 35/00* (2013.01); *G01N 35/04* (2013.01)

(58) Field of Classification Search
CPC ........ G01N 11/04; G01N 11/00; G01N 15/05; G01N 2223/301
See application file for complete search history.

(56) References Cited

U.S. PATENT DOCUMENTS 3,520,179 A * 7/1970 Reed .................. G01N 11/06
73/54.04
4,028,929 A * 6/1977 Bohm .................. G01N 11/06
73/54.04
(Continued)

FOREIGN PATENT DOCUMENTS

JP       2007-127468 A   5/2007
KR    10-2002-063571 A   8/2002
(Continued)

OTHER PUBLICATIONS

PCT/KR2016/013623 International Preliminary Report on Patentability, dated May 29, 2018. (Year: 2018).*

*Primary Examiner* — David A Rogers
(74) *Attorney, Agent, or Firm* — Novick, Kim & Lee, PLLC; Sang Ho Lee

(57) ABSTRACT

The present invention relates to a portable blood viscosity measurement apparatus, and the present invention includes a case portion which is movable and includes an upper case and a lower case which are installed in a foldable manner, a blood sample injection unit that is installed in the upper case, mixes blood in a blood sample container, and automatically supplies the blood, a blood viscosity measurement unit that is installed in the upper case and measures a blood viscosity which is supplied from the blood sample injection unit, and (Continued)

a data processing unit that is installed in the lower case, analyzes a value which is measured by the blood viscosity measurement unit, and calculates blood viscosity.

13 Claims, 8 Drawing Sheets

(51) Int. Cl.
*G01N 33/49* (2006.01)
*G01F 23/292* (2006.01)
*G01N 35/00* (2006.01)
*G01N 35/04* (2006.01)

(56) References Cited

U.S. PATENT DOCUMENTS

| | | | | |
|---|---|---|---|---|
| 4,156,570 A * | 5/1979 | Wardlaw | ............... | G01N 15/042 356/36 |
| 4,554,821 A * | 11/1985 | Kiesewetter | ............ | G01N 11/06 73/54.07 |
| 4,677,845 A * | 7/1987 | Izumi | ............... | G01N 11/04 137/92 |
| 4,691,558 A * | 9/1987 | Vinson | ............ | G01N 11/00 73/64.41 |
| 4,779,976 A * | 10/1988 | Levine | ............ | G01N 15/05 356/39 |
| 4,858,127 A * | 8/1989 | Kron | ............ | G01N 11/00 73/54.09 |
| 5,142,899 A * | 9/1992 | Park | ............... | G01N 11/06 73/54.04 |
| 5,224,375 A * | 7/1993 | You | ............... | G01N 11/06 118/723 E |
| 5,333,497 A * | 8/1994 | Br nd | ............... | G01F 3/36 73/219 |
| 5,447,440 A * | 9/1995 | Davis | ............... | G01N 11/04 422/73 |
| 5,616,855 A * | 4/1997 | Ball | ............... | B01L 7/02 73/54.43 |
| 5,837,885 A * | 11/1998 | Goodbread | ............ | B82Y 15/00 73/32 A |
| 6,077,234 A * | 6/2000 | Kensey | ............... | A61B 5/02035 600/573 |
| 6,152,888 A * | 11/2000 | Kensey | ............... | A61B 5/02035 600/573 |
| 6,200,277 B1 * | 3/2001 | Kensey | ............... | A61B 5/02035 600/573 |
| 6,261,244 B1 * | 7/2001 | Kensey | ............... | A61B 5/02035 600/573 |
| 6,322,524 B1 * | 11/2001 | Kensey | ............... | A61B 5/02035 600/573 |
| 6,428,488 B1 * | 8/2002 | Kensey | ............... | A61B 5/02035 600/573 |
| 6,745,615 B2 * | 6/2004 | Kensey | ............... | A61B 5/02035 73/54.04 |
| 6,907,772 B2 * | 6/2005 | Kensey | ............... | A61B 5/02035 73/54.04 |
| 7,541,191 B2 * | 6/2009 | Duic | ............... | G01N 15/05 422/68.1 |
| 7,600,416 B2 * | 10/2009 | Lin | ............... | G01N 13/02 73/64.48 |
| 8,499,618 B2 * | 8/2013 | Doo | ............... | G01N 35/1011 73/54.01 |
| 9,791,386 B2 * | 10/2017 | Henning | ............... | G01N 11/04 |
| 10,078,060 B2 * | 9/2018 | Geier | ............... | G01N 23/223 |
| 10,168,265 B2 * | 1/2019 | Dwarakanath | ............ | E21B 43/16 |
| 10,209,171 B2 * | 2/2019 | Vanapalli | ............... | G01N 11/04 |

FOREIGN PATENT DOCUMENTS

| KR | 10-0958447 B1 | 5/2010 |
|---|---|---|
| KR | 10-2013-0057242 A | 5/2013 |
| KR | 10-1476923 B1 | 12/2014 |

\* cited by examiner

PORTABLE BLOOD VISCOSITY MEASUREMENT APPARATUS

TECHNICAL FIELD

The present invention relates to a portable blood viscosity measurement apparatus, and more particularly, to a portable blood viscosity measurement apparatus capable of measuring blood viscosity unhindered by place and an additional apparatus using a small amount of whole blood obtained from a human body or an animal.

BACKGROUND ART

Blood viscosity is a physical value that assays flow resistance of the blood in a blood vessel, and specifically, can be divided into a whole blood viscosity and a plasma viscosity. An abnormal increase in the blood viscosity causes an increase in a shear stress and the flow resistance acting on an inner wall of the blood vessel, thereby, significantly increasing a risk of developing acute cardiovascular disease and microvascular disease. In addition, the plasma viscosity is used to diagnose inflammation in the body and is one of main causes increasing the whole blood viscosity.

The whole blood viscosity shows flow characteristics in which viscosity continuously changes depending on a systolic phase and a diastolic phase of the heart because the viscosity decreases when blood flows at a high speed (when a shear rate is high) and the viscosity increases when blood flows at a low speed (when the shear rate is low) due to complex effects of red blood cells and plasma proteins in whole blood. Fluids with such flow characteristics are called non-Newtonian fluid and it is necessary to accurately measure the whole blood viscosity for a total shear rate (for example, 1 to 1,000 s-1) so as to accurately grasp the non-Newtonian flow characteristics of the blood.

The plasma viscosity measured by using plasma obtained by separating the red blood cells from the whole blood, does not vary with the shear rate and is constant unlike the whole blood viscosity. Fluid with such flow characteristics is called Newtonian fluid.

Presently, the blood viscosity is measured by a precisely devised large equipment once a blood sample obtained and transmitted to the measurement room. It is impossible to measure the blood viscosity at a desired place and time due to an absence of a measurement technique capable of performing an on-site and real time inspection proposed in the present patent. Previously, the viscosity of blood was measured by using the following methods.

First, a U-shaped double-vertical-tube/single-capillary viscometer measures viscosity by measuring a difference in height, which is reduced by gravity, by providing a height difference between blood contained in the two vertical capillary tubes, and has the following advantages.

The U-shaped double-vertical-tube/single-capillary viscometer uses a disposable U-shaped tube, because it is easy to use in clinical applications since there is no need to clean, no risk of infection, capable of viscosity measurement for 1 to 1000 s^-1 shear rate range, and can measure both the whole blood viscosity and the plasma viscosity can be measured.

However, there are problems where the U-shaped double-vertical-tube/single-capillary viscometer causes an error in viscosity measurement in the low shear rate range less than 1 s^-1 due to a structural constraint, hardly measures a viscosity value lower than or equal to 1 cP due to characteristics of a measurement algorithm, requires a large amount of whole blood of 3 mL or more in order to measure the whole blood viscosity, and requires a lot of whole blood of 6 mL or more so as to measure the plasma viscosity after plasma is separated from the whole blood. In addition, there are problems in which a separate dyeing process is required for measuring the plasma viscosity, and it is difficult to perform point-of-care testing due to inconvenient transport caused by a large size and a heavy weight because a fixed type method is used.

The Brookfield viscometer measures viscosity by measuring a torque acting on a plate due to fluid while rotating the fluid put in a chamber in a state where a spring is connected to the plate, has the following advantages. The Brookfield viscometer is capable of performing the measurement using a small amount of blood of approximately 0.5 mL, and can measure both the whole blood viscosity and the plasma viscosity. However, since the Brookfield viscometer measures viscosity only for a specific shear rate, it is practically impossible to measure the whole blood viscosity with respect to the total shear rate in case of the whole blood viscosity, and because the Brookfield viscometer does not have a disposable measurement structure, once the measurement is performed, a measurer has to clean the viscometer to remove blood by hand for the next measurement, and furthermore there is a risk of infection caused by blood during the cleaning process, it is difficult to use the viscometer. In addition, it is difficult to perform point-of-care testing due to inconvenient transport caused by a large size and a heavy weight because a fixed type method is used.

The Ostwald glass capillary plasma viscometer measures viscosity by measuring time when plasma of 10 mL passing through a vertical glass tube including a capillary tube and has an advantage of not using any electronic device and can be used at any location. However, in order to obtain plasma of 10 mL required for measuring the plasma viscosity, a large amount of whole blood of 20 mL is required, the whole blood viscosity cannot be measured, remeasurement is performed after the capillary tube is cleaned once the measurement is performed, and since a diameter of the capillary tube is less than 1 mm, it is impossible to clean the capillary tube realistically. In addition, the Ostwald glass capillary plasma viscometer is exposed to the risk of infection caused by the blood during the cleaning process, and thus, the viscometer cannot be used in the clinic, and since the measurer directly measures a height change time using a stopwatch, there is a problem that a large error occurs depending on the measurer.

DETAILED DESCRIPTION OF THE INVENTION

Technical Problem

An object of the present invention is to provide a portable blood viscosity measurement apparatus capable of independently measuring viscosity of blood by using a small amount of whole blood obtained from a human body or an animal regardless of a place and an additional device.

Technical Solution

According to an embodiment of the present invention, a portable blood viscosity measurement apparatus includes a case portion which is movable and includes an upper case and a lower case which are installed in a foldable manner; a blood sample injection unit that is installed in the upper case, mixes blood in a blood sample container, and automatically supplies the blood; a blood viscosity measurement unit that is installed in the upper case and measures a blood viscosity which is supplied from the blood sample injection unit; and a data processing unit that is installed in the lower case, analyzes a value which is measured by the blood viscosity measurement unit, and calculates blood viscosity. The blood viscosity measurement unit includes a detachable cartridge attached to the upper case and includes two vertical support portions in which spaces are respectively formed and which are connected to each other in a U-shape; a lower connector that is mounted on a lower portion of the cartridge; first and second vertical tubes that are respectively inserted into the two vertical support portions; a capillary tube that is inserted into the lower connector; an auxiliary tube path that is formed in the lower connector and connects the second vertical tube to the capillary tube; a valve unit which is formed in the lower connector, supplies blood that is supplied from the blood sample injection unit to the first vertical tube, causes the blood that is flowed into the first vertical tube to be supplied to the capillary tube, and in which a flow path is variable so as to supply blood in the first and second vertical tubes and the capillary tube to the blood sample injection unit side, and first and second sensor units that are adjacent to the first and second vertical tubes and sense a position of blood in the first and second vertical tubes.

The two vertical support portions may respectively include incising portion that can visually identify heights of the blood in the first and second vertical tubes.

The portable blood viscosity measurement apparatus may further include a cartridge transport unit that is in close contact with the cartridge or the lower connector and transports the cartridge and the lower connector so as to protrude from the upper case.

The portable blood viscosity measurement apparatus may further include a heater unit that is installed in the upper case, is disposed on a rear surface of the cartridge, and supplies heat to the cartridge.

The heater may include a heat generation unit that generates heat, and a heat supply tube that is formed in a shape corresponding to the two vertical support portions of the cartridge.

The two vertical support portions may include predetermined regions of the heater unit sides which are incised such that the heat of the heater unit is supplied.

The blood sample injection unit may include a container mounting portion on which the blood sample container is mounted; a needle portion that includes first and second needles that are inserted into the blood sample container; a pump portion that provides a pneumatic pressure to the first needle; and a rotation portion that periodically rotates the container mounting portion and the needle portion at a predetermined angle.

The portable blood viscosity measurement apparatus may further include a connection tube that is formed in the upper case and connects the second needle to the valve unit.

The data processing unit may control the pump portion, the rotation portion, and the valve unit, operate the rotation portion to mix blood in the blood sample container if the blood sample container is mounted on the container mounting portion, drive the pump portion so as to inject air into the blood sample container through the first needle and control such that the blood is supplied to the valve unit through the second needle, and rotate the valve unit to be connected to the first vertical tube and the connection tube before the pump portion is driven.

The portable blood viscosity measurement apparatus may further include a support portion that is disposed between the upper case and the lower case such that the upper case is supported perpendicularly to the lower case.

The portable blood viscosity measurement apparatus may further include a level meter that measures a horizontal level of the lower case with respect to a floor.

The portable blood viscosity measurement apparatus may further include at least three horizontal adjustment units that are installed in the lower case, are installed to be in close contact with the floor, and whose heights are variable.

The portable blood viscosity measurement apparatus may further include a barcode recognition unit that recognizes a barcode which is attached to the blood sample container or the lower connector and that transmits the recognized data to the data processing unit.

Advantageous Effects of the Invention

The portable blood viscosity measurement apparatus according to an embodiment of the present invention has an advantage capable of performing blood viscosity testing on the spot by including a blood sample injection unit, a blood viscosity measurement unit, and a data processing unit which are provided in a mobile case portion.

In addition, the portable blood viscosity measurement apparatus according to the embodiment of the present invention has an advantage that a blood collection burden is reduced and viscosity of blood of a small animal as well as a human body can be measured since a small amount of blood (less than or equal to approximately 1.5 ml) is used.

In addition, the portable blood viscosity measurement apparatus according to the embodiment of the present invention can provide ease of an operation by installing a program for measuring the viscosity of blood in a data measurement unit.

The portable blood viscosity measurement apparatus according to the embodiment of the present invention has an advantage that a cartridge can be easily separated from a blood viscosity measurement unit and the blood supplied to the cartridge can be automatically injected and restored.

In addition, the portable blood viscosity measurement apparatus according to the embodiment of the present invention can uniformly supply heat to the blood viscosity measurement unit, thereby, reducing an error according to the temperature when measuring the blood viscosity.

BEST MODE OF THE INVENTION

Figure 1:
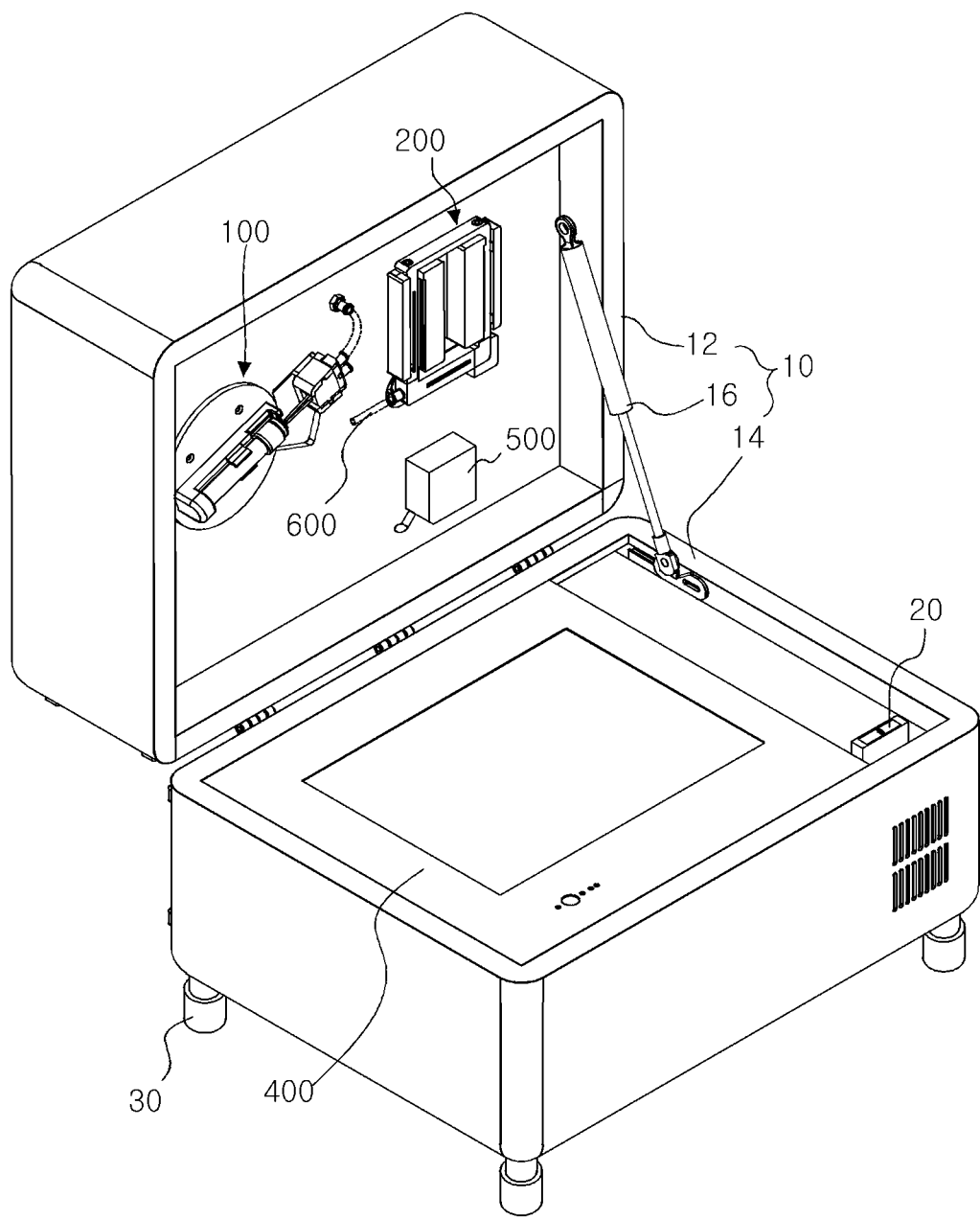
FIG. 1 is a perspective view illustrating a portable blood viscosity measurement apparatus according to an embodiment of the present invention.

The present invention provides a portable blood viscosity measurement apparatus including a case portion which is movable and includes an upper case and a lower case which are installed in a foldable manner; a blood sample injection unit that is installed in the upper case, mixes blood in a blood sample container, and automatically supplies the blood; a blood viscosity measurement unit that is installed in the upper case and measures a viscosity of blood which is supplied from the blood sample injection unit; and a data processing unit that is installed in the lower case, analyzes a value which is measured by the blood viscosity measurement unit, and calculates viscosity of the blood. The blood viscosity measurement unit includes a cartridge that is detachably attached to the upper case and includes two vertical support portions in which spaces are respectively formed and which are connected to each other in a U-shape; a lower connector that is mounted on a lower portion of the cartridge; first and second vertical tubes that are respectively inserted into the two vertical support portions; a capillary tube that is inserted into the lower connector; an auxiliary tube path that is formed in the lower connector and connects the second vertical tube to the capillary tube; a valve unit which is formed in the lower connector, supplies blood that is supplied from the blood sample injection unit to the first vertical tube, causes the blood that is flowed into the first vertical tube to be supplied to the capillary tube, and a flow path is variable so as to supply blood in the first and second vertical tubes and the capillary tube to the blood sample injection unit side, and first and second sensor units that are adjacent to the first and second vertical tubes and sense a position of blood in the first and second vertical tubes.

MODE OF THE INVENTION

Hereinafter, a description of the present invention with reference to the drawings is not limited to a specific embodiment, various modifications may be applied thereto, and various embodiments may be employed. In addition, it is to be understood that the following description is intended to cover all modifications, equivalents, and replacements falling within the spirit and scope of the present invention.

In the following description, the terms first, second, and the like are used to describe various configuration elements, and are not limited in their meaning, and are used only for the purpose of distinguishing one configuration element from another configuration element.

The same reference numerals or symbols used throughout the specification denote the same configuration elements.

As used herein, a singular form includes plural referents unless the context clearly dictates otherwise. In addition, it is to be understood that the terms "include", "comprise", "have", and the like are intended to designate the presence of features, integers, steps, operations, configuration elements, components, or combinations thereof which are described in the specification, and do not preclude the presence or addition of one or more other features, numbers, steps, operations, configuration elements, components or combinations thereof.

Hereinafter, embodiments of the present invention will be described in detail with reference to FIGS. 1 to 8 attached herewith.

FIG. 1 is a perspective view illustrating a portable blood viscosity measurement apparatus according to an embodiment of the present invention.

Referring to FIG. 1, the portable blood viscosity measurement apparatus according to the present invention includes a case portion 10, a blood sample injection unit 100, a blood viscosity measurement unit 200, a heater unit 700, and a data processing unit 400.

Specifically, the case portion 10 is a bag-shaped case that a user can easily move. The case portion 10 includes the blood sample injection unit 100, the blood viscosity measurement unit 200, the heater unit 700, and the data processing unit 400, and protects the blood sample injection unit 100, the blood viscosity measurement unit 200, the heater unit 700, and the data processing unit 400 from an external impact or the like. A handle for movement can be attached to the case portion 10.

The case portion 10 includes an upper case 12, a lower case 14, and a support portion 16.

The upper case 12 has a space in which the blood sample injection unit 100, the blood viscosity measurement unit 200, and the heater unit 700 are mounted. The upper case 12 may include an outlet so as to prevent the case from overheating because heat generated in the heater unit 700 stays inside the case. It is preferable that the outlet is also formed in the lower case 14. At this time, the outlet formed in the lower case 14 is used to discharge heat generated in the data processing unit 400 to the outside.

The lower case 14 includes the data processing unit 400 therein. The lower case 14 includes a level meter 20 for vertically aligning first and second vertical tubes 240 and 250 of the blood viscosity measurement unit 200 included in the upper case 12 with a ground surface. A commonly used level meter can be used as the level meter 20. The level meter 20 can be installed at a lower right portion as illustrated in FIG. 1 such that a user can easily use and in consideration of disposition of the data processing unit 400. However, the position is not limited to this, and the level meter can be installed in a region that can be recognized by the user.

At least three horizontal adjustment units 30 whose heights are changed to be horizontal can further be provided on a lower surface of the lower case 14. In the embodiment of the present invention, four horizontal adjustment units 30 are provided at the respective corners of the lower case 14.

The lower case 14 can be provided with a battery or power conversion means that stores power supplied to the blood sample injection unit 100, the blood viscosity measurement unit 200, the heater unit 700, the data processing unit 400, and the like.

As illustrated in FIG. 1, the support portion 16 is disposed on the right sides of the upper case 12 and the lower case 14, and supports the upper case 12 to the lower case 14 such that the upper case 12 and the lower case 14 are perpendicular to each other. The support portion 16 is installed in a foldable manner, and when reaching the maximum length, the upper case 12 and the lower case 14 are perpendicular to each other. In particular, when blood viscosity is measured, the support portion 16 is fixed by a separate button or fixing means such that a length of the support portion 16 is not varied. When the work is completed, the length of the support portion 16 can be varied so as to be folded by an operation of an operator.

If a blood sample container 50 is mounted, the blood sample injection unit 100 mixes blood in the blood sample container 50 by making a reciprocating motion at a set angle so as to prevent red blood cells contained in the blood sample container 50 from sinking on a floor to cause a measurement error. The blood sample injection unit 100 continuously performs the mixing during the waiting time for measuring the viscosity, and supplies the blood in the blood sample container 50 to the blood viscosity measurement unit 200 when the viscosity measurement is started. A specific configuration of the blood sample injection unit 100 will be described again with reference to FIG. 2.

The blood viscosity measurement unit 200 includes two vertical tubes for measuring the viscosity of blood supplied from the blood sample container 50, and a capillary tube disposed between the two vertical tubes. The blood viscosity measurement unit 200 uses a method in which, when the blood moves from one vertical tube to the other vertical tube via a capillary tube, time when heights of the blood in the two vertical tubes are equal is measured to measure viscosity of non-neutronic blood. At this time, two sensors for measuring the heights of the blood in the two vertical tubes are provided, and each sensor transmits values measured during a predetermined time to the data processing unit 400. The blood viscosity measurement unit 200 will be described in more detail with reference to FIG. 3 to FIG. 7.

A connection tube 600 can be further provided between the blood sample injection unit 100 and the blood viscosity measurement unit 200. The connection tube 600 can perform a tube function for supplying blood from the blood sample injection unit 100 to the blood viscosity measurement unit 200 when the blood sample injection unit 100 and the blood viscosity measurement unit 200 are separated from each other, and an opposite case thereof can be made. The connection tube 600 is installed on the upper case 12.

In case where an interval between the blood sample injection unit 100 and the blood viscosity measurement unit 200 is small and thereby a needle portion (120 of FIG. 2) provided in the blood sample injection unit 100 come in closely contact with a valve unit 230 of the blood viscosity measurement unit 200, it is not necessary to use the connection tube 600.

Figure 8:
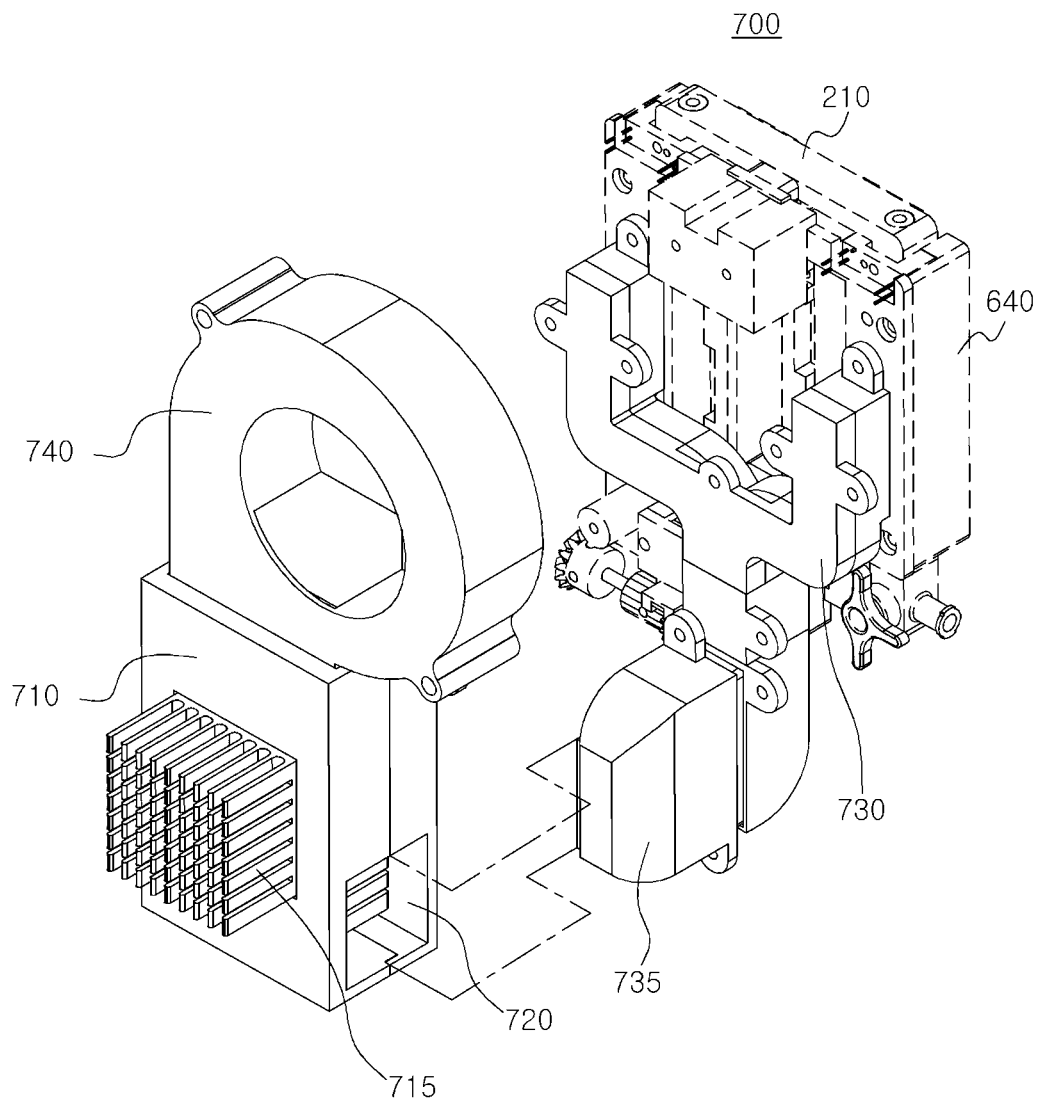
FIG. 8 is a perspective view illustrating a heater unit included in the blood viscosity measurement apparatus.

Although not illustrated in FIG. 1, the heater unit 700 is installed on a rear surface or a back surface of the blood viscosity measurement unit 200 as illustrated in FIG. 8, and supplies heat to the blood viscosity measurement unit 200. The heater unit 700 can supply hot air to the vertical tube to uniformly raise a temperature within a short time before measurement is made. The heater unit 700 can continuously supply heat so that the same temperature can be maintained even during viscosity measurement is made by the blood viscosity measurement unit 200. Description thereof will be made again with reference to FIG. 8.

The data processing unit 400 receives information from first and second sensors 270 and 280 provided in the blood viscosity measurement unit 200 and calculates the blood viscosity by using a previously stored calculation formula or algorithm. The data processing unit 400 is mounted to the lower case 14. The data processing unit 400 can perform overall control for performing processing for measuring the blood viscosity. That is, the data processing unit 400 performs a function of a controller or a control unit.

The data processing unit 400 includes a touch-type display such that a user can easily measure the blood viscosity by touching commands displayed on the display. In the blood viscosity measurement, the blood is automatically supplied to the blood viscosity measurement unit 200 in response to a start command displayed on the touch-type display, a value of the blood viscosity is displayed on the display, and the blood used for the measurement is recovered to the blood sample container 50.

The data processing unit 400 can control a pump portion 130, a rotation portion 160, and a valve unit 230, which will be described below. The data processing unit 400 operates the rotation portion 160 to mix the blood in the blood sample container 50 and then drives the pump portion 130 to inject air into the blood sample container 50 such that the blood is supplied to the blood viscosity measurement unit 200. In addition, the data processing unit 400 can control various configuration elements in the apparatus. Description thereof will be made in connection with description of each configuration element.

Meanwhile, the blood viscosity measurement apparatus according to the embodiment of the present invention may further include a barcode recognition unit 500.

The barcode recognition unit 500 automatically recognizes a barcode attached to a lower end of a lower connector 220 coupled with a U-shaped cartridge 210 and transmits the recognized value to the data processing unit 400. In addition, the barcode recognition unit 500 can recognize a barcode attached to the blood sample container 50. The barcode recognition unit 500 is installed in the upper case 12 such that a user can easily recognize the barcode but is not limited to this. The barcode recognition unit 500 can be installed in the lower case 14 or can be connected through wire or wireless to the data processing unit 400.

Hereinafter, main configuration elements of the blood viscosity measurement apparatus will be described with reference to FIGS. 2 to 8.

Figure 2:
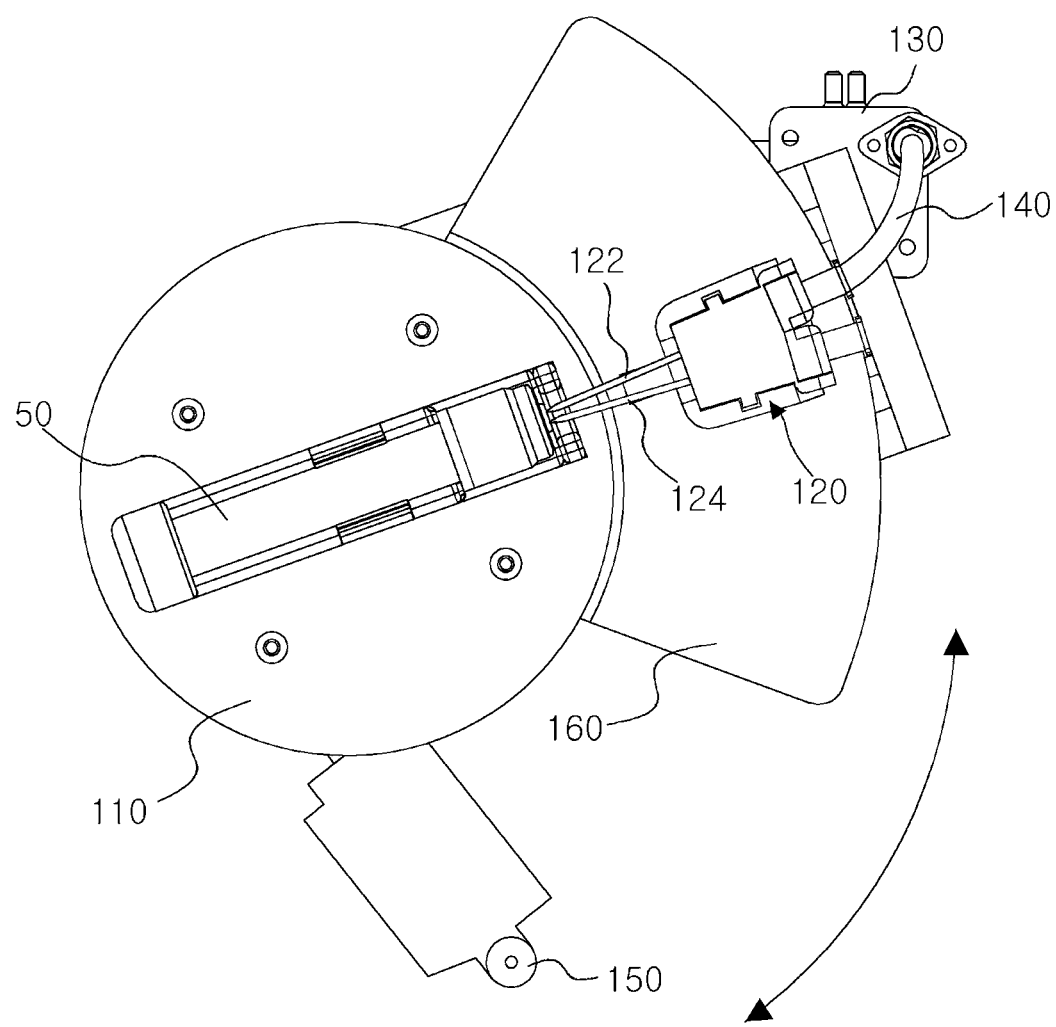
FIG. 2 is a view illustrating a blood sample injection unit of the blood viscosity measurement apparatus illustrated in FIG. 1.

FIG. 2 is a view illustrating the blood sample injection unit of the blood viscosity measurement apparatus illustrated in FIG. 1.

Referring to FIG. 2, the blood sample injection unit 100 can include a container mounting portion 110, a needle portion 120, the pump portion 130, and the rotation portion 160.

Specifically, the container mounting portion 110 includes a circular plate-shaped member which is rotatable and is formed in a shape corresponding to the blood sample container 50 mounted on the plate-shape member. At this time, one end of the container mounting portion 110 supports the end of the blood sample container 50 and the other end thereof is formed to be open such that first and second needles 122 and 124 of the needle portion 120 are inserted into the blood sample container 50. In addition, the container mounting portion 110 can include separate fixing means for fixing the blood sample container 50.

The needle portion 120 is spaced apart from the container mounting portion 110 and can be installed on an upper surface of the rotation portion 160. The needle portion 120 includes the first and second needles 122 and 124 and tubes respectively connected to the first and second needles 122 and 124 are formed. Here, the needle portion 120 is formed such that two nozzles are exposed to the outside as illustrated in FIG. 2. At this time, one of the two nozzles can be connected to the first needle 122, and the other nozzle can be connected to the connection tube 600 described above. An air connection tube 140 connects the first needle 122 to the pump portion 130.

The rotation portion 160 rotates the container mounting portion 110 at a predetermined interval to mix the blood in the blood sample container 50. The rotation portion 160 is formed in a fan shape on the outside of the container mounting portion 110 where the container mounting portion 110 is installed as illustrated in FIG. 2. The rotation portion 160 includes the needle portion 120. In the present invention, the rotation portion 160 is provided to rotate within a range of approximately 45 degrees, but is not limited thereto. At this time, the rotation portion 160 is coupled with the container mounting portion 110 and rotates at the same time to shake the blood sample container 50 within a predetermined range, and thereby the red blood cells in the blood are prevented from being deposited on the bottom of the blood sample container.

When the blood sample injection unit 100 is fixed to the upper case 12 and supplies blood to the blood viscosity measurement unit 200, a stopper 150 can be further installed to fix a position of the blood sample injection unit 100.

The stopper 150 is fixed to the upper case 12 and come into contact with one surface of the rotation portion 160 such that the nozzle connected to the second needle 124 of the needle portion 120 comes into close contact with the connection tube 600 and thereby a position thereof is not deviated.

The pump portion 130 can supply air or suck the air through a control signal of the data processing unit 400. In case where the pump portion 130 supplies air, the air is supplied to the blood sample container 50 through the first needle 122, and thereby, an internal pressure raises. Thereafter, the blood in the blood sample container 50 is discharged through the second needle 124 and is supplied to the blood viscosity measurement unit 200.

In contrast to this, in case where the air is sucked by the pump portion 130, the pressure in the blood sample container 50 is reduced, and thereby, the blood of the blood viscosity measurement unit 200 is restored into the blood sample container 50.

As described above, blood can be automatically supplied to the blood viscosity measurement unit 200 through the pump portion 130, or the blood of the blood viscosity measurement unit 200 can be restored into the blood sample container 50. Accordingly, the restored blood can be easily used for other blood tests, and risk of contamination at the time of reusing is remarkably reduced. In addition, discarding the blood can be easily performed.

In the embodiment of the present invention, the blood in the blood viscosity measurement unit 200 can be restored in another container by using a manifold or the like, even if the pump portion 130 is not used.

Figure 3:
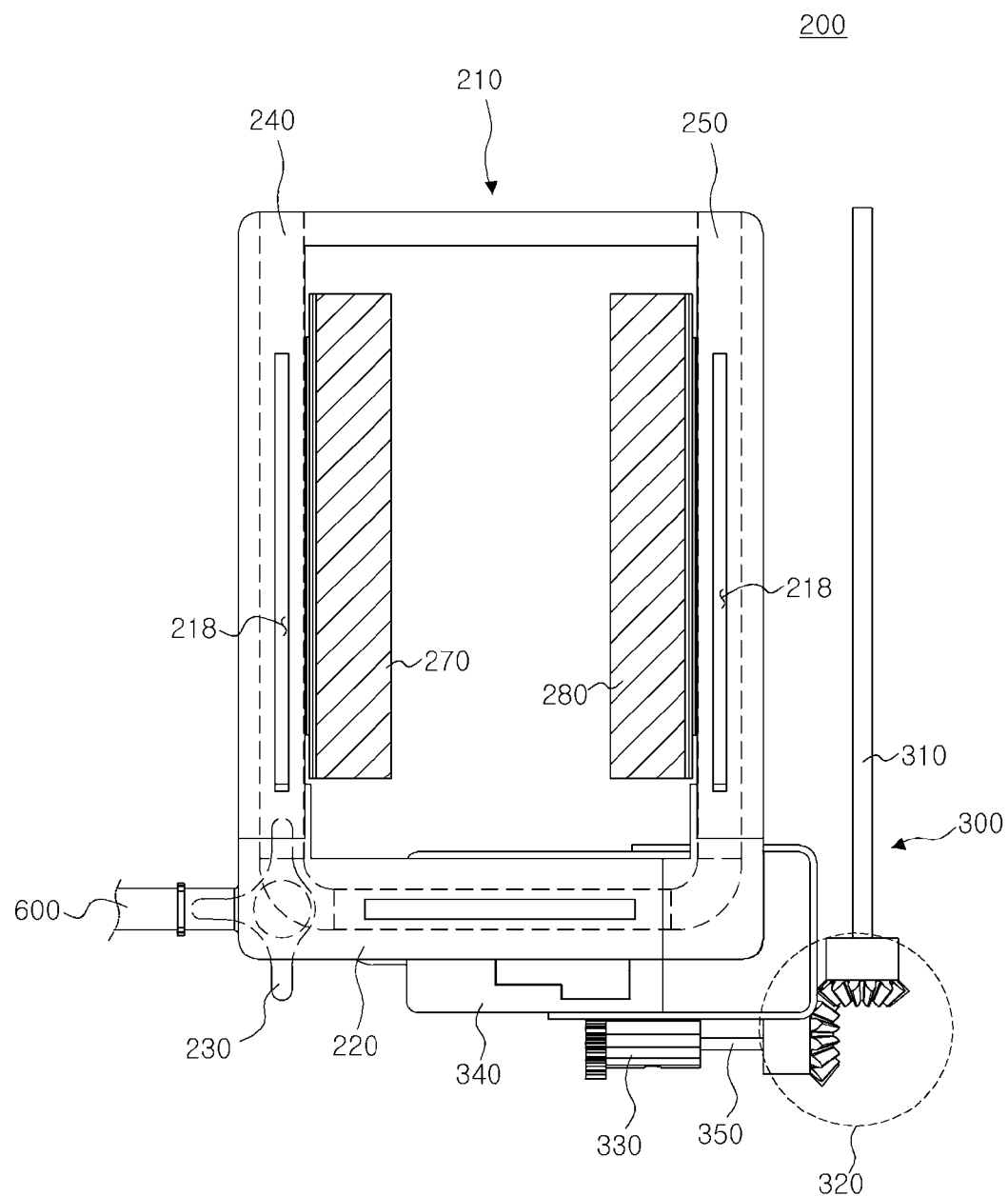
FIG. 3 is a detailed view of a blood viscosity measurement unit of the blood viscosity measurement apparatus illustrated in FIG. 1.
Figure 4:
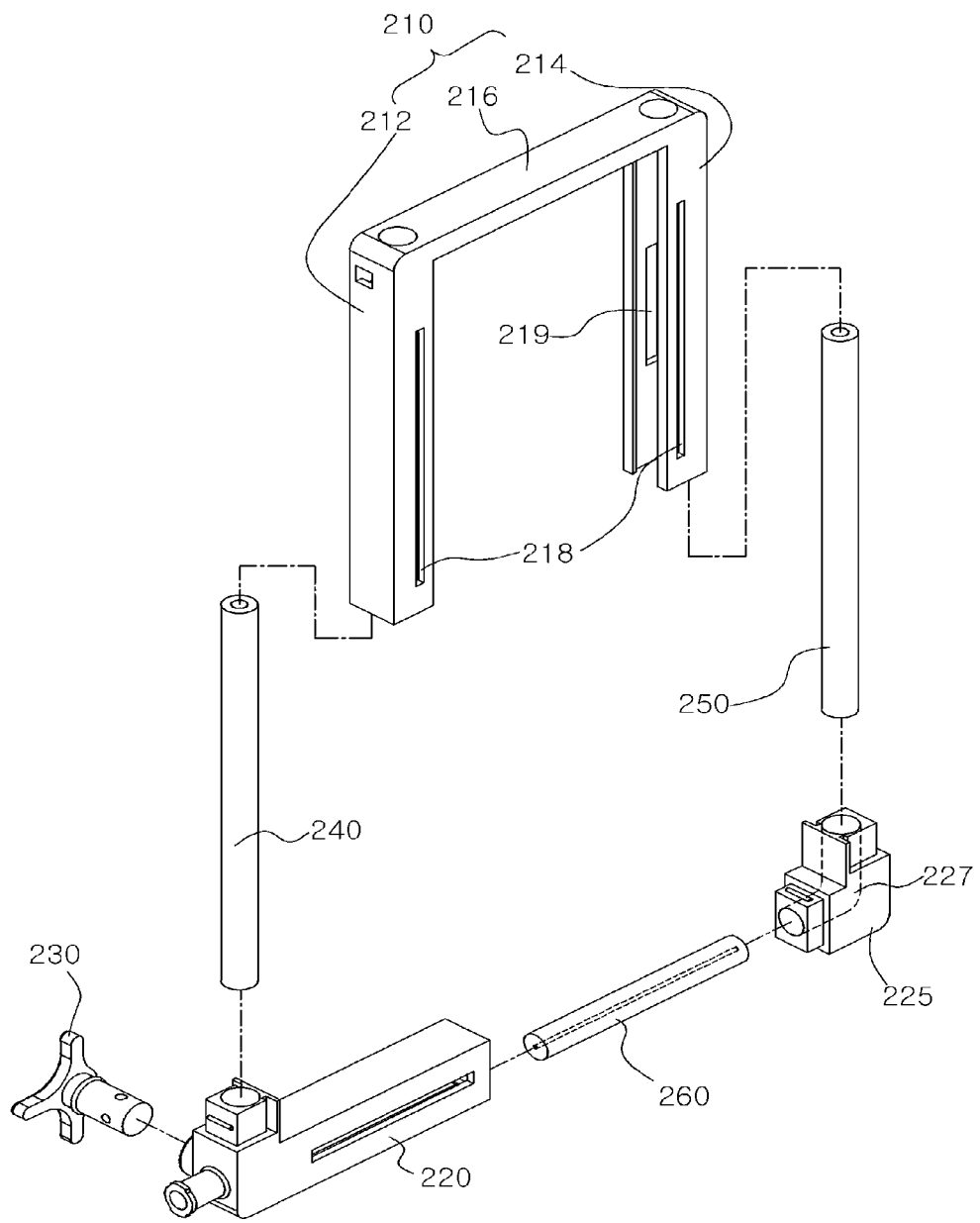
FIG. 4 is an exploded perspective view illustrating a cartridge of the blood viscosity measurement unit illustrated in FIG. 3.

FIG. 3 is a detailed view of the blood viscosity measurement unit of the blood viscosity measurement apparatus illustrated in FIG. 1, FIG. 4 is an exploded perspective view illustrating a cartridge of the blood viscosity measurement unit illustrated in FIG. 3, FIG. 5 through FIG. 7 is a view illustrating an operation state of a valve unit illustrated in FIG. 3.

Figure 5:
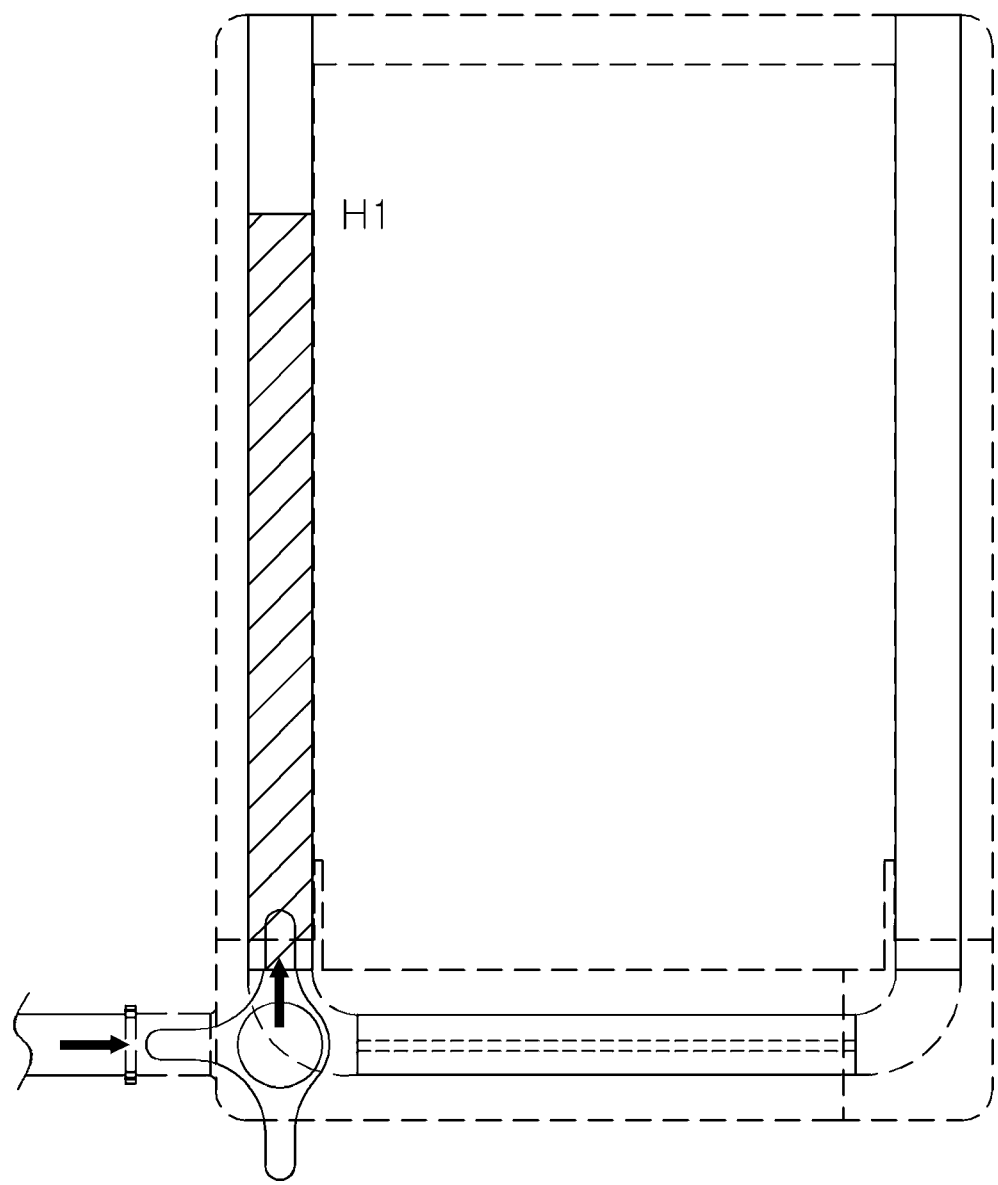
FIG. 5 through FIG. 7 are views illustrating an operation state of a valve unit illustrated in FIG. 3.
Figure 7:
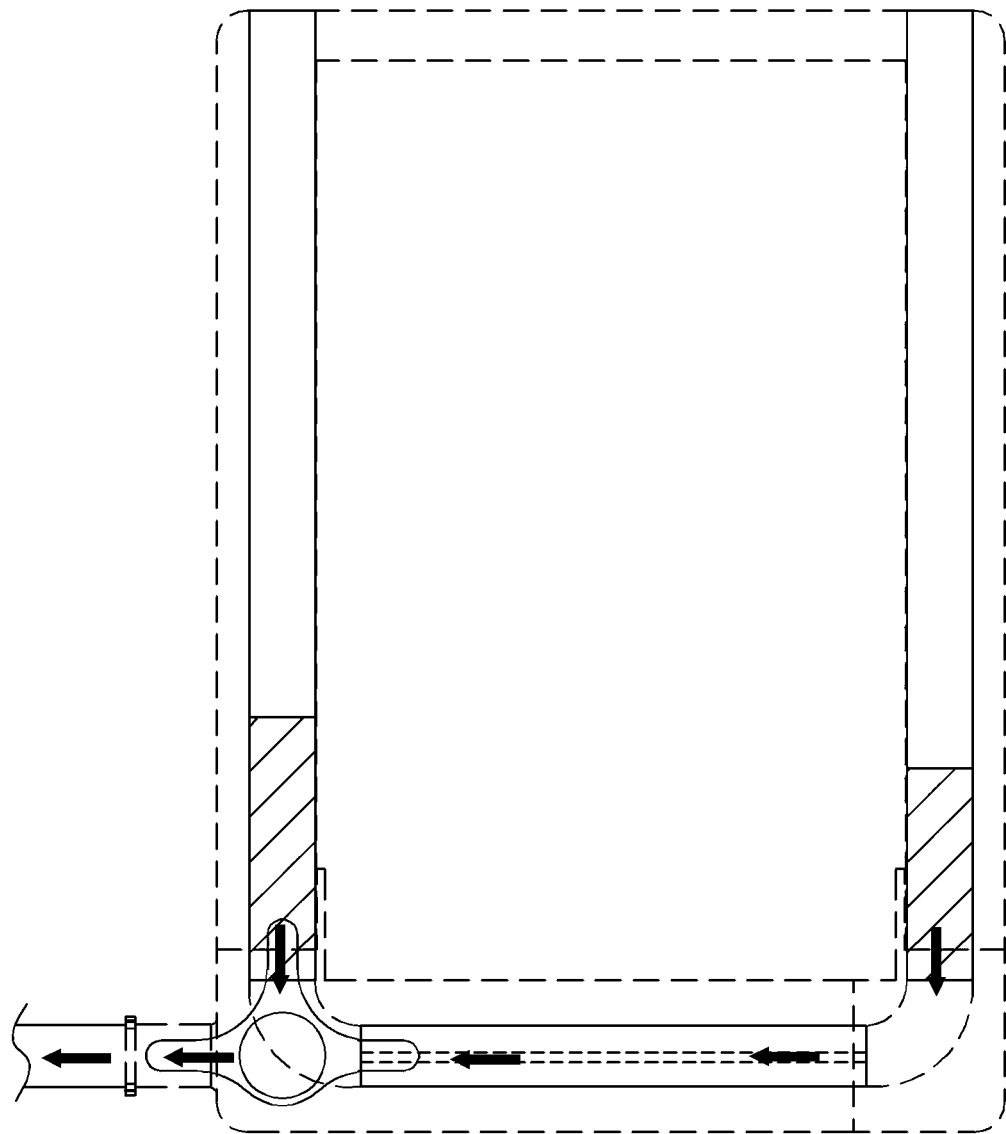

Referring to FIGS. 3, 5, and 7, the blood viscosity measurement unit 200 includes the cartridge 210, the first and second vertical tubes 240 and 250, a capillary tube 260, the lower connector 220, the first sensor 270, the second sensor 280, and the valve unit 230.

Specifically, the cartridge 210 has a shape in which two vertical support portions 212 and 214 are connected in a "U" shape by a connection portion 216. The two vertical support portions 212 and 214 of the cartridge 210 have spaces in which the first vertical tube 240 and the second vertical tube 250 are respectively inserted. The two vertical support portions 212 and 214 of the cartridge 210 are incised and formed in a lengthwise incision such that the first and second vertical tubes 240 and 250 are mounted in the spaces. The first and second sensors 270 and 280 for measuring blood heights of the first and second vertical tubes 240 and 250 are disposed on side surfaces of the two vertical support portions 212 and 214, respectively. The cartridge 210 are coated with various colors or are formed of various materials so as to reduce a measurement error by blocking light incident from the outside when the first and second sensors 270 and 280 measure changes of the blood heights. At this time, incising portions 218 can be formed on front surfaces of the two vertical supports 212 and 214 so as to visually observe heights of the blood in the first and second vertical tubes 240 and 250.

Meanwhile, openings 219 can be formed on the rear surfaces of the two vertical support portions 212 and 214 so as to accommodate heat supplied from the heater unit 700.

The lower connector 220 is mounted on a lower portion of the cartridge 210. The lower connector 220 can be incised in the longitudinal direction such that the capillary tube 260 is mounted. The lower connector 220 includes an auxiliary lower connector 225 coupled to the lower connector 220, and the auxiliary lower connector 225 has an auxiliary tube path 227, which connects the second vertical tube 250 to the capillary tube 260, therein. As illustrated in FIG. 4, the lower connector 220 can be formed such that a portion where the first vertical tube 240 is coupled with the second vertical tube 250 is separated and is assembled. A structure can be formed in which the capillary tube 260 is installed in a state where the lower connector 220 is separated, the lower connector and the capillary tube are assembled with each other, and the lower connector and the capillary tube are assembled with the cartridge 210.

The valve unit 230 is coupled with the lower connector 220. The valve unit 230 is a three-way valve. The valve unit 230 operates such that the first vertical tube 240 and the connection tube 600 are connected to each other, operates such that the first vertical tube 240 and the capillary tube 260 are connected to each other, or operates such that the first vertical tube 240, the connection tube 600, and the capillary tube 260 are connected to each other.

The valve unit 230 can operate in three states in response to a control signal of the data processing unit 400.

First, as illustrated in FIG. 5, when the blood is supplied to the blood viscosity measurement unit 200, the valve unit 230 operates such that a flow path is formed only between the connection tube 600 and the first vertical tube 240. At this time, the blood supplied from the blood sample container 50 rises to a height H1 of the first vertical tube 240.

Figure 6:
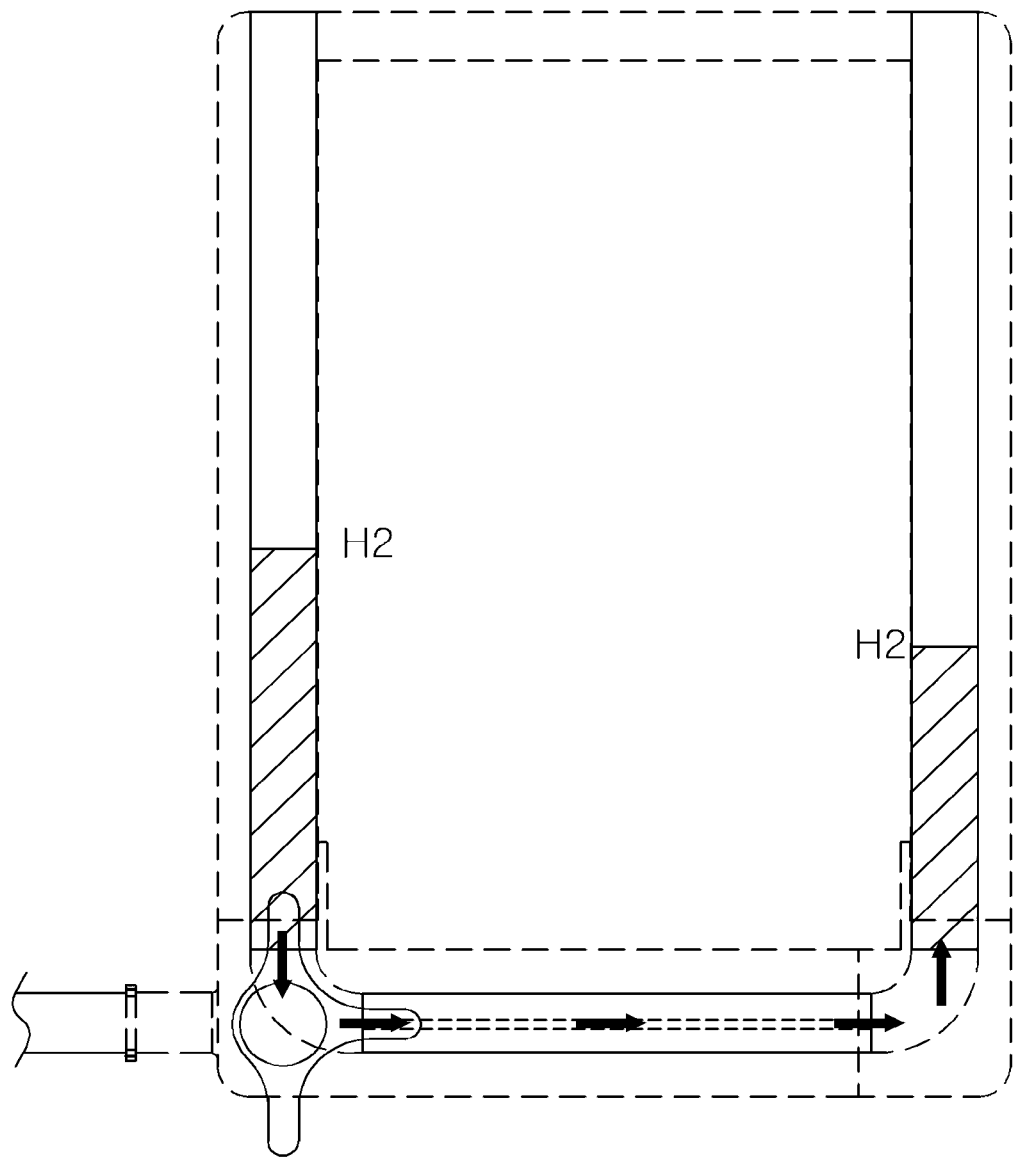

Thereafter, as illustrated in FIG. 6, the valve unit 230 operates such that a flow path is formed only between the first vertical tube 240 and the capillary tube 260. At this time, the blood supplied to the first vertical tube 240 is supplied to the second vertical tube 250 through the capillary tube 260 by gravity. The valve unit 230 maintains this state until the blood heights of the first vertical tube 240 and the second vertical tube 250 are equal to each other.

Subsequently, if the blood heights of the first vertical tube 240 and the second vertical tube 250 are equalized and thereby the viscosity measurement is completed, a flow path is formed between the connection tube 600, the first vertical tube 240, and the capillary tube 260 so as to restore the blood of the first vertical tube 240, the capillary tube 260, and the second vertical tube 240 through the connection tube 600, as illustrated in FIG. 7.

As described above, as the valve unit 230 is operated, the blood is supplied to the first vertical tube 240 when measuring blood viscosity. After the blood viscosity is measured, the blood in the first and second vertical tubes 240 and 250 and the capillary tube 260 can be restored in the blood sample container 50.

The first and second sensors 270 and 280 can measure height of the blood of the first and second vertical tubes 240 and 250 and provide the measured data to the data processing unit 400. For this, an optical sensor such as a contact image sensor (CIS) can be used as each of the first and second sensors 270 and 280. In addition, a CCD sensor or the like can be used as each of the first and second sensors 270 and 280.

Transparency and a degree of contamination of the first and second vertical tubes 240 and 250 can be automatically diagnosed in advance by using the first and second sensors 270 and 280.

Meanwhile, a cartridge transport unit 300 may be further provided for inserting and discharging the cartridge 210.

The cartridge transport unit 300 can include a gear unit 320, a main rotation shaft 310, a transport shaft 350, a transport binding unit 340, and a rotation transport unit 330.

The main rotation shaft 310 rotates by receiving power. The main rotation shaft 310 can discharge the cartridge 210 during a forward rotation and insert the cartridge 210 during a reverse rotation. An opposite case thereof is also possible.

The gear unit 320 transmits a rotation force of the main rotation shaft 310 to the transport shaft 350. In particular, the gear unit 320 can be a Bevel gear or the like in consideration of an installation direction of the main rotation shaft 310 and an installation direction of the transport shaft 350.

The transport shaft 350 is coupled with the gear unit 320 and rotates by receiving power of the main rotation shaft 310. The rotation transport unit 330 is coupled with the transport shaft 350 to rotate, and thereby, the cartridge 210 is transported. At this time, the transport binding unit 340 can be provided on the rear surface of the lower connector 220 such that the cartridge 210 can be easily transported.

A plurality of teeth can be formed in the rotation transport unit 330, and grooves are formed on one surface of the transport unit 340 such that the rotation transport unit 330 is engaged with the teeth, and the transport binding unit 340 moves up and down by the grooves of the transport binding unit 340 as the rotation transport unit 330 rotates.

FIG. 4 illustrates that the gear unit 320, the transport shaft 350, the transport binding unit 340, and the rotation transport unit 330 are disposed on the rear surface of the lower connector 220, but the present invention is not limited to this. The cartridge also has the same configuration as the gear unit 320, the transport shaft 350, the transport binding unit 340, and the rotation transport unit 330, and the cartridge 210 and the lower connector 220 can move the cartridge 210 up and down at the same time.

FIG. 8 is a perspective view illustrating the heater unit provided in the blood viscosity measurement apparatus.

As illustrated in FIG. 8, the heater unit 700 can include a heat generation unit 710 and a heat supply tube 730.

The heat generation unit 710 includes heat generation means such as a coil for generating the heat, or generates heat by using other means instead of the coil.

The heat supply tube 730 is installed on the rear surface of the cartridge 210, and is formed in a Y shape in particular. The heat supply tube 730 supplies the heat supplied from the heat generation unit 710 to the cartridge 210. At this time, it is preferable that the heat supply tube 730 is formed to be open to a size corresponding to an opening 219 of the cartridge 210 described above such that the heated air is directly supplied into the cartridge 210.

The heat generation unit 710 includes a discharge portion 720 and the discharge portion 720 can be connected through a transfer portion 735 connected to the heat supply tube 730. In addition, a circulation tube 740 may be further formed on the heat generation unit 710 such that the heated air circulates and moves on the discharge portion 720 side. The hot air raised through the circulation tube 740 is supplied to the discharge portion 720.

The heat generation unit 710 can further include a heat sink 715 that discharges heat to the outside. The heat sink 715 prevents the heat generation unit 710 from overheating.

Meanwhile, although not illustrated in FIGS. 3 and 8, a temperature sensor that measures the temperature inside the cartridge can be further provided. The temperature sensor is attached to the cartridge to directly or indirectly measure an internal temperature of the cartridge 210 and provide measured data to the data processing unit 400. The data processing unit 400 can control the heater unit 700 so as to maintain the internal temperature of the cartridge 210 at a predetermined temperature through information input from the temperature sensor.

While the preferred embodiments of the present invention are described in the above description, it is to be understood that the invention is not limited to the above-described embodiments and various changes and modifications can be made. In addition, it is to be understood that, if a changed embodiment and a modified embodiment also include a technical idea of the present invention described in the scope of claims which will be described below, the changed embodiment and the modified embodiment are included in the scope of the present invention.

The invention claimed is:

1. A portable blood viscosity measurement apparatus comprising:
   a case portion which is movable;
   a blood sample injector that mixes blood in a blood sample container, and automatically supplies the blood;
   a blood viscosity measurement assembly that measures a blood viscosity which is supplied from the blood sample injector; and
   a data processor that analyzes a value which is measured by the blood viscosity measurement assembly, and calculates the blood viscosity,
   wherein the blood viscosity measurement assembly includes:
      a cartridge that is detachably attached to the case and includes two vertical support portions, wherein each of the two vertical support portions defines a space therein and the two vertical support portions are connected to the cartridge to form a U-shape;
      a lower connector that is mounted on the two vertical support portions;
      a first vertical tube and a second vertical tube that are capable of being respectively inserted into the space of the two vertical support portions;
      a capillary tube that is inserted into the lower connector;
      an auxiliary tube path that is formed in the lower connector and connects the second vertical tube to the capillary tube;
      a valve which is disposed in the lower connector, supplies the blood that is supplied from the blood sample injector to the first vertical tube, and causes the blood that is flowed into the first vertical tube to be supplied to the capillary tube, wherein the valve has a configuration to change a flow path and supplies the blood from the first and second vertical tubes and the capillary tube to the blood sample injector, and
      a first sensor and a second sensor that are disposed adjacent to the first and second vertical tubes and sense a position of the blood in the first and second vertical tubes, respectively.

2. The portable blood viscosity measurement apparatus of claim 1, wherein the two vertical support portions respectively include incising portion and visually identify heights of the blood in the first and second vertical tubes.

3. The portable blood viscosity measurement apparatus of claim 1, further comprising:
a cartridge transport assembly that comes into close contact with the cartridge or the lower connector, and transports the cartridge and the lower connector to be protruded from the case.

4. The portable blood viscosity measurement apparatus of claim 1, wherein the case includes an upper case and a lower case which are installed in a foldable manner, and wherein the case further comprises a support portion that is disposed between the upper case and the lower case and the upper case is supported perpendicularly to the lower case.

5. The portable blood viscosity measurement apparatus of claim 1, further comprising:
a barcode recognition assembly that recognizes a barcode which is attached to the blood sample container or the lower connector and that transmits the recognized data to the data processor.

6. The portable blood viscosity measurement apparatus of claim 1, further comprising:
a heater that is installed in the case, is disposed on a rear surface of the cartridge, and supplies heat to the cartridge.

7. The portable blood viscosity measurement apparatus of claim 6, wherein the heater includes:
a heat generation assembly that generates heat; and
a heat supply tube that is disposed in a shape corresponding to the two vertical support portions of the cartridge.

8. The portable blood viscosity measurement apparatus of claim 7, wherein the two vertical support portions include predetermined regions which are disposed to face the heater and are incised to receive the heat from the heater.

9. The portable blood viscosity measurement apparatus of claim 1, wherein the blood sample injector includes:
a container mounting portion on which the blood sample container is mounted;
a needle assembly that includes a first needle and a second needle which are inserted into the blood sample container;
a pump that provides a pneumatic pressure to the first needle; and
a rotation portion that periodically rotates the container mounting portion and the needle portion at a predetermined angle.

10. The portable blood viscosity measurement apparatus of claim 9, further comprising:
a connection tube that is disposed in the case and connects the second needle to the valve.

11. The portable blood viscosity measurement apparatus of claim 10, wherein the data processor controls the pump, the rotation portion, and the valve, operates the rotation portion to mix the blood in the blood sample container if the blood sample container is mounted on the container mounting portion, drives the pump and injects air into the blood sample container through the first needle and controls that the blood is supplied to the valve through the second needle, and rotates the valve and connects the first vertical tube and the connection tube before the pump is driven.

12. The portable blood viscosity measurement apparatus of claim 1, further comprising:
a level meter that measures a horizontal level of the case with respect to a floor.

13. The portable blood viscosity measurement apparatus of claim 12, further comprising:
at least three horizontal adjustment assemblies that are installed in the case to support the case on the floor, and whose heights are configured to be changed.

* * * * *